US008512687B2

(12) United States Patent
Lambert et al.

(10) Patent No.: US 8,512,687 B2
(45) Date of Patent: Aug. 20, 2013

(54) OIL IN WATER EMULSION COMPRISING NSAIDS AND QUATERNARY AMMONIUM HALIDES

(75) Inventors: Grégory Lambert, Chatenay Malabry (FR); Laura Rabinovich-Guilatt, Kadima (IL); Frédéric Lallemand, Fresnes (FR); Jean-Sébastien Garrigue, Verrieres le Buisson (FR); Betty Philips, Antony (FR)

(73) Assignee: Novagali Pharma SA, Evry (FR)

( * ) Notice: Subject to any disclaimer, the term of this patent is extended or adjusted under 35 U.S.C. 154(b) by 298 days.

(21) Appl. No.: 12/846,310

(22) Filed: Jul. 29, 2010

(65) Prior Publication Data
US 2011/0021443 A1    Jan. 27, 2011

Related U.S. Application Data

(63) Continuation-in-part of application No. 11/774,838, filed on Jul. 9, 2007, now abandoned.

(51) Int. Cl.
*A61K 31/74* (2006.01)
(52) U.S. Cl.
USPC ...................................... 424/78.04
(58) Field of Classification Search
USPC ...................................... 424/70.04
See application file for complete search history.

(56) References Cited

U.S. PATENT DOCUMENTS

| 4,454,151 | A | 6/1984 | Waterbury |
| 5,110,493 | A | 5/1992 | Cherng-Chyi et al. |
| 6,245,349 | B1 * | 6/2001 | Yiv et al. ........................ 424/450 |
| 2006/0100288 | A1 | 5/2006 | Bague et al. |
| 2007/0134339 | A1 | 6/2007 | Jenkins et al. |

FOREIGN PATENT DOCUMENTS

| EP | 0390071 | 10/1990 |
| EP | 0696452 | 2/1996 |
| EP | 1688144 | 8/2006 |
| WO | 2007042262 | 4/2007 |

OTHER PUBLICATIONS

Klang et al., Influence of Emulsion Droplet Surface Charge on Indomethacin Ocular Tissue Distribution, Pharmaceutical Development and Technology, vol. 5, No. 4, pp. 521-532, 2000.*
European search report in corresponding EP 07112104, Dec. 19, 2007.
Abdulrazik M et al., "Ocular delivery of cyclosporin A II. Effect of submicron emulsion's surface charge on ocular distribution of topical cyclosporin A", Sciences techniques et pratiques STP pharma sciences, vol. 11, No. 6, 2001, pp. 427-432, XP008033036.
S.H. Klang et al., "Evaluation of a positively charged submicron emulsion of piroxicam on the rabbit corneum healing process following alkali burn", Journal of controlled release, Elsevier, 1999, pp. 19-27.

* cited by examiner

*Primary Examiner* — Lezah Roberts
*Assistant Examiner* — Nannette Holloman
(74) *Attorney, Agent, or Firm* — Young & Thompson

(57) ABSTRACT

Oil-in-water emulsion including a non-steroidal anti-inflammatory drug and a quaternary ammonium halide useful for the prevention and treatment of inflammation in the eye, and process for manufacturing thereof.

23 Claims, 1 Drawing Sheet

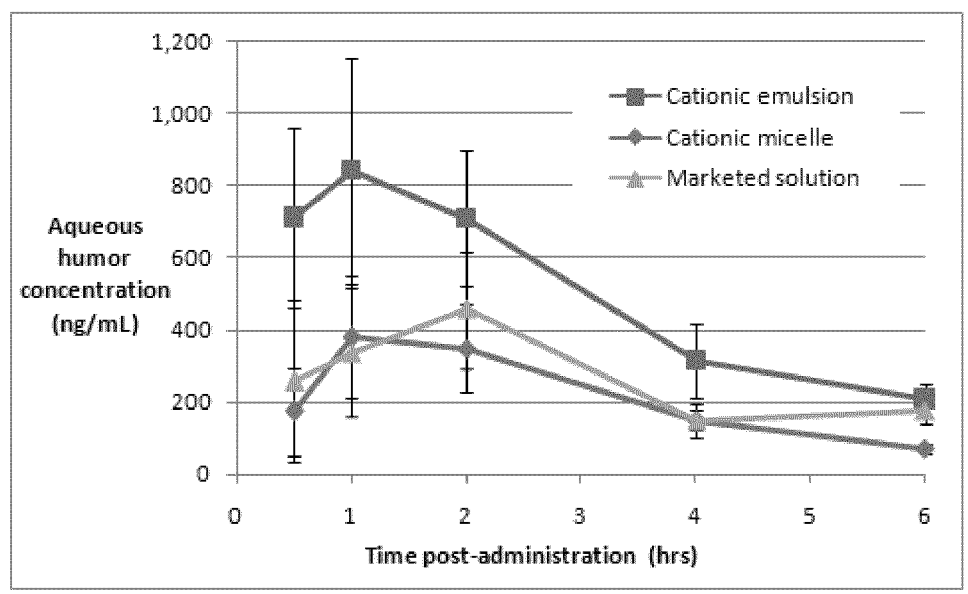

OIL IN WATER EMULSION COMPRISING NSAIDS AND QUATERNARY AMMONIUM HALIDES

CROSS REFERENCE TO RELATED APPLICATIONS

This application is a continuation-in-part of co-pending application Ser. No. 11/774,838 filed on Jul. 9, 2007. The entire contents of each of the above-identified applications are hereby incorporated by reference.

FIELD OF THE INVENTION

This invention relates to pharmaceutical, including ophthalmic compositions comprising non-steroidal anti-inflammatory drugs (NSAIDs), more preferably to ophthalmic emulsions being useful for the treatment of eye conditions.

This invention also relates to oil-in-water emulsions comprising NSAIDs and further including at least one quaternary ammonium compound as cationic agent.

BACKGROUND

The topical use of NSAIDs in the treatment of ophthalmic diseases was first taught in U.S. Pat. No. 4,454,151. This US patent disclosed efficacious formulations with $NaH_2PO_4H_2O$, $Na_2PO_4H_2O$, NaCl, benzalkonium chloride (BAK) and sterilized water. However, these formulations were found to not have the stability required for shelf life in formulations.

Ocufen Ophthalmic solution, a non-patented medicament launched in 1988, is the first NSAID (flurbiprofen) approved by the FDA for ophthalmic use, and incorporates thimerosal as its preservative system. Thimerosal is an irritating compound (approximately 49% mercury by weight), and is known for its teratogenic side effects. New generations of ophthalmic formulations deprived from thimerosal are therefore needed.

U.S. Pat. No. 5,110,493 disclosed improved and stable ophthalmic solutions (but no emulsions) including NSAID and using BAK as preservative. This formulation comprises 0.001% to 10% of NSAID, 0.001% to 1% of preservative such as BAK, 0.001% to 1% of surfactant such as octoxynol 40, excipients and water. This formulation was shown to be stable for at least the minimum reasonable shelf life of such products. However, bioavailability is poor: typical dosage ranges for this formulation to treat an eye condition is disclosed to be about 2-10 drops of 0.1% solution of NSAID per day.

This raises the problem of bioavailability of topically instilled drugs such as NSAIDs. Most of these NSAIDs exhibit complex ocular formulations problem due to aqueous solubility limitations. Therefore, attempts have been made to improve ocular bioavailability of NSAIDs by designing new colloidal delivery systems based either on nanoparticles, and negatively or positively charged submicron emulsions.

Examples of such emulsions are disclosed in Klang et al (Journal of Controlled Release, 1999, 57:19-27): NSAID 0.1%, MCT 8.5%, Lipoid E80 1.2%, stearylamine 0.3%, alpha-tocopherol 0.02%, poloxamer 188 1%, glycerol 2.2.5% and water.

The Applicant worked on different ophthalmic emulsions for NSAIDs in order to obtain an emulsion having a better stability and providing a better ocular bioavailability of NSAIDs.

In US2006/0100288, the Applicant suggests that NSAID could be added in oil-in-water emulsions. However, the Applicant did not provide any working example.

The Applicant further worked on long chain quaternary ammonium compounds such as BAK, and noticed that the length of the alkyl chain was important with regards to the function performed by the quaternary ammonium compounds in an oil-in-water emulsion containing NSAIDs: acting on the length of the alkyl chain resulted in enhancing or reducing the cationic power of the quaternary ammonium compounds. Without wanting to be linked by any theory, the Applicant observed on working on oil-in-water emulsions containing NSAIDs, that long chain alkyl quaternary ammonium compounds were preferentially localized at the oil/water interface of the emulsions, resulting in (1) emulsions with higher zeta potential and (2) more stable emulsions.

In addition, the Applicant observed that an emulsion comprising NSAID and a quaternary ammonium halide in which the nitrogen atom is substituted by one or more alkyl group having at least 12, preferably 14 or 16, more preferably 16 carbon atoms provides a better ocular bioavailability compared to others formulations, which is of importance and resulted in the design of therapeutic emulsions having a content in oil of less than 6%, preferably of 5% or less, thus less irritating than the prior art emulsion.

Moreover, the Applicant noticed that the process for manufacturing NSAID containing emulsions at physiological pH (i.e. pH ranging from 6.8 to 7.4) was not leading to stable emulsion.

Therefore, stability of NSAID containing emulsions appeared to be a technical issue, for which no solution was provided in the prior art.

SUMMARY OF THE INVENTION

Therefore, the goal of this invention is to provide a stable oil-in-water emulsion comprising a non-steroidal anti-inflammatory drug and a quaternary ammonium halide in which the nitrogen atom is substituted by one or more alkyl group having at least 12 carbon atoms, preferably 14 or 16 carbon atoms. By stable, is meant an emulsion that keeps a positive zeta potential overtime.

BRIEF DESCRIPTION OF THE DRAWINGS

FIG. 1 refers is a graph showing bioavailability of the emulsions of the invention. This graph shows the aqueous humour concentration of flurbiprofen overtime after administration.

DETAILED DESCRIPTION OF THE INVENTION

Zeta Potential

Zeta potential measures a physical property which is exhibited by any particle in suspension. Zeta potential can be used to predict behaviour of the suspension in different environments, to optimize the formulations of suspensions and emulsions as well as to predict overtime stability.

In order to avoid the emulsion droplets to merge one with the other and form droplets of successively increasing size, it is necessary to confer repulsive forces to the particles. One of the means to confer repulsive forces to a colloidal system is by electrostatic or charge stabilization. Electrostatic or charge stabilization has the benefits of stabilizing a system by simply altering the concentration of ions in the system.

This is a reversible and inexpensive process.

There might by many origins of this surface charge depending upon the nature of the particle and its surrounding medium but the most important mechanisms are the ionisation of surface groups or the adsorption of charged ions.

The interaction of particles in polar liquids is not governed by the electrical potential at the surface of the particle, but by the effective potential of the particle and its associated ions. To utilize electrostatic control of dispersions, it is the zeta potential of the particle that must be measured rather than its surface charge. Charged particles will attract ions of opposite charge in the dispersant. Ions close to the surface are strongly bound; those further away form a more diffuse region. Within this region is a notional boundary, known as the slipping plane, within which the particle and ions act as a single entity. The potential at the slipping plane is known as the zeta potential. It has long been recognised that the zeta potential is a very good index of the magnitude of the interaction between colloidal particles and measurements of zeta potential are commonly used to assess the stability of colloidal systems. The zeta potential measured in a particular system is dependent on the chemistry of the surface, and also of the way it interacts with its surrounding environment. Therefore zeta potential must always be studied in a well defined environment (specifically pH and ionic strength).

According to the invention, said emulsion is useful for ophthalmic purposes.

Definitions

In the meaning of this invention,

"Cationic emulsions" are emulsions having a positive zeta potential, preferably a zeta potential higher to 10 mV;

"long chain alkyl" are alkyl moieties having at least 12 carbon atoms, preferably at least 14 carbon atoms, more preferably at least 16 carbon atoms;

n-alkyl dimethyl benzyl ammonium chloride also called benzalkonium chloride (hereinafter also referred to as BAK)

"BAK C12" refers to benzododecinium chloride (CAS 139-07-1);

"BAK C14" refers to myristalkonium chloride (CAS 139-08-2);

"BAK C16" refers to cetalkonium chloride (CAS 122-18-9);

"MCT" means medium chain triglycerides; for the experimentation, TCM™ (Société des Oléagineux, France) was the MCT used;

"stable" refers to a composition that keeps a positive zeta potential overtime, which means that the composition passes the stability test hereunder described.

Stability test consists in measuring the stability of the emulsion zeta potential under thermal stress conditions.

Zeta potential of the emulsion is measured at T=0, i.e. as soon as the emulsion has been prepared, the obtained value being named $Z_0$. Glass vials (Type I) of 10 ml effective capacity containing between 5-10 ml of emulsion and sealed under nitrogen atmosphere (without bubbling) are stored at 80° C.

Then at T=15 days the zeta potential $Z_{15d}$ is measured.

The value $\delta = Z_{15d} - Z_0$ is then calculated.

For each measurement of the zeta potential, it is operated as follows:

The zeta potential of the emulsion droplet surface is determined by electrophoretic mobility in an apparatus such as a Malvern Zetasizer 2000 (Malvern Instruments, UK) equipped with suitable software and calibrated with the supplied standard.

The emulsion is diluted in double distilled water if needed in order to obtain the scattering intensity allowing optimal particle detection. The sample count rate should be between 100 to 1000 KCps, in homodyne detection (if heterodyne detection is used, the contribution of the reference beam should be deduced). Three consecutive measurements are performed at 25° C. using a constant cell drive of 150 mV. The electrophoretic mobility is converted into zeta potential values through the Smoluchowsky equation, using the dielectric constants and viscosity of water. The measured value corresponds to the average of the 3 obtained values.

It is considered that the emulsion meets zeta potential stability Test if δ is less than the standard error of measurements, preferably less than 10 mV, and even more preferably less than 5 mV.

"Flurbiprofen" means a compound selected from 2-((3-fluoro-4-phenyl)phenyl)propanoic acid and salts thereof, preferably the sodium salt, and hydrates thereof and flurbiprofen anhydride; the term "flurbiprofen" in the meaning of this invention also includes flurbiprofen derivatives, especially flurbiprofen acid derivatives wherein the acid function is protected by any suitable protecting group, or flurbiprofen amide derivatives. The term "flurbiprofen" in the meaning of this invention may designate (1) racemic flurbiprofen, i.e. a mixture of (S)-flurbiprofen and (R)-flurbiprofen, and includes not only a mixture of (S)-flurbiprofen and (R)-flurbiprofen at a molar ratio of 50:50, but also a mixture of (S)-flurbiprofen and (R)-flurbiprofen at a molar ratio from 20:80 to 80:20, preferably from 30:70 to 70:30, (2) or pure or enriched enantiomer forms, such as for example (R)-flurbiprofen or (S)-flurbiprofen, preferably (S)-flurbiprofen as well as pharmaceutical acceptable salts.

This invention thus relates to an oil-in-water emulsion comprising at least one NSAID and at least one quaternary ammonium halide, more preferably ammonium chloride or bromide, in which the nitrogen atom of the ammonium group is substituted by at least one or only one alkyl group having at least 12 carbon atoms, more preferably by one alkyl group having at least 14 carbon atoms, more preferably by one alkyl group having at least 16 carbon atoms.

According to an embodiment, the non-steroidal anti-inflammatory drug is chosen among ketorolac, ketoprofen, salicylate, indomethacin, ibuprofen, flurbiprofen, suprofen, piroxicam, COX2 inhibitors, diclofenac, nimesulide, nepafenac; antineoplastics, cisplatin, mitomycin and fluorouracil.

Advantageously, said non-steroidal anti-inflammatory drug is flurbiprofen, ketoprofen and/or ibuprofen.

According to an embodiment, the therapeutic oil-in-water emulsion of the invention comprises 0.001% to 10% w/w preferably 0.01% to 1% w/w, more preferably 0.02% to 0.05% w/w of a non-steroidal anti-inflammatory drug, such as for example flurbiprofen, ibuprofen and ketoprofen, preferably flurbiprofen, in weight by total weight of the emulsion.

According to a first embodiment the amount of non-steroidal anti-inflammatory drug in the emulsion of the invention ranges from 0.03 to 0.9% w/w.

According to a second embodiment, the amount of non-steroidal anti-inflammatory drug in the emulsion of the invention ranges from 0.03 to 0.7% w/w.

The emulsions comprising the non-steroidal anti-inflammatory drug should be prepared at a pH lower than 7.00, and lower than the pKa of the drug.

In the case of ibuprofen and ketoprofen, for example, the pKa of ibuprofen is 4.91 and the pKa of ketoprofen is 4.45. A pH from about 3.00 to about 5.00 produces desirable emulsions for these two drugs. As a result, these emulsions are stable during the sterilization step and have good emulsion characteristics, such as a small monomodal droplet size distribution (around 100-150 nm) and positive zeta potentials. Although stable emulsions may be prepared with ibuprofen and ketoprofen at a pH from 5.00 to 6.00, this increase in the pH leads to a higher droplet size distribution which also becomes multimodal with micronic populations. Additionally, as pH increases, zeta potential decreases.

One would expect a similar effect of pH for other non-steroidal anti-inflammatory-profens, such as flurbiprofen.

In one embodiment of the invention, the emulsion is prepared at a pH lower than 7, and then buffered at a physiological pH (i.e. pH ranging from 6.8 to 7.4). In a particular embodiment, said emulsion is buffered by adding a buffering agent selected from the group comprising phosphate buffer, tris buffer, acetate buffer or citrate buffer.

According to an embodiment, the quaternary ammonium halide is a C16-alkyl quaternary ammonium halide, preferably C16-alkyl benzyl dimethyl ammonium chloride.

Advantageously, the ammonium halide is BAK C12, BAK C14, BAK C16 or a mixture thereof. According to an embodiment, the only ammonium halide of the emulsion is BAK C14 or BAK C16 or a mixture thereof.

According to an embodiment, the therapeutic oil-in-water emulsion of the invention is cationic. By cationic oil-in water emulsion is understood an oil-in-water emulsion having a positive zeta potential. In this embodiment, the emulsion of the invention has a positive zeta potential.

Advantageously, the emulsion of the invention keeps a positive zeta potential overtime. By overtime is meant over a period of at least 15 days.

According to an embodiment, the therapeutic oil-in-water emulsion of the invention comprises 0.001 to 0.1%, preferably 0.005 to 0.05%, more preferably 0.01 to 0.03% in weight of ammonium halide by total weight of the emulsion.

The therapeutic oil-in-water emulsion according to the invention further comprises an oil phase preferably comprising MCT, castor oil, soybean oil or any suitable vegetal or mineral oil, surfactants preferably chosen among at least one of tyloxapol, poloxamer, preferably poloxamer 188, tocopherol, polyethylene glycols, and polysorbate, sorbitan monolaurate, polyethoxylated castor oil and optionally antioxidants and/or isotonicity or osmotic agents preferably chosen among at least one of glycerol, glycerin and mannitol. According to an embodiment, the therapeutic oil-in-water emulsion of the invention comprises 0.1 to 5%, preferably 0.5 to 4%, more preferably 1 to 3% in weight of oil, preferably MCT, by total weight of the emulsion. According to an embodiment, the therapeutic oil-in-water emulsion of the invention comprises 0.01 to 2%, preferably 0.05 to 1%, more preferably 0.1 to 0.5% in weight of surfactants to the total weight of the emulsion. According to an embodiment, the emulsion of the invention includes at least one surfactant in the oily phase, preferably in an amount of 0.1 to 0.5%, preferably 0.3% in weight to the total weight of the emulsion and at least one surfactant in the aqueous phase preferably in an amount of 0.02 to 0.2%, preferably 0.1% in weight to the total weight of the emulsion. Preferred surfactants are tyloxapol, poloxamer and sorbitan monolaurate.

According to an embodiment, the therapeutic oil-in-water emulsion of the invention has a mean droplet size of 100 to 500 nm, preferably 150 to 400 nm, more preferably 110 to 250 nm.

According to an embodiment, the therapeutic oil-in-water emulsion of the invention is preserved.

According to another embodiment, the oil-in-water emulsion of the invention is unpreserved.

In one embodiment of the invention, the terms "preserved" or "unpreserved" refer to antimicrobial preservation. According to an embodiment, the emulsion of the invention is preserved when it includes an antimicrobial agent. According to another embodiment, the emulsion of the invention is unpreserved when it is free of any preservative agent.

This invention also relates to a medicament comprising a therapeutic oil-in-water emulsion of the invention and pharmaceutically acceptable excipient.

This invention also relates to the use of an oil-in-water emulsion according to the invention for the manufacture of a medicament for the treatment of an eye disease caused by, associated with or accompanied by inflammatory processes. In the meaning of the invention, eye diseases caused by, associated with or accompanied by inflammatory processes means a wide variety of ocular conditions such as for example glaucoma, ocular inflammatory conditions such as keratitis, uveitis, intra-ocular inflammation, allergy and dry eye syndrome, ocular infections, ocular allergies, ocular infections, retinal oedema, macular oedema, diabetic retinopathy or any trauma caused by eye surgery or eye injury, LASIK surgery, peri surgery (pre, per and/or post) for prevention and treatment of pain and inflammation.

Advantageously, the medicament is administrated less than 4 times a day, preferably less than twice a day and more preferably less than once a day. According to an embodiment, each administration is of 1-5 drops per eye. According to an embodiment, each drop has a volume of 30 to 70 µl, preferably about 50 µl. According to an embodiment, the medicament may be both curative and preventative. Where applied, for example, pre-surgically or immediately post-traumatically, i.e. before inflammation develops, the emulsion of the invention prevents development of inflammation. When applied directly to the eye suffering from any of the named ophthalmic diseases, it suppresses or attenuates or limits already existing inflammatory processes. This invention thus relates to a method for preventing inflammation and/or for treating inflammation when applied to an eye, comprising administering to a patient in need thereof a the therapeutic oil-in-water emulsion of the invention or a medicament containing such.

This invention also relates to a therapeutic ophthalmic oil-in-water emulsion or a medicament containing such, in a unitary dosage form, for a single use. Advantageously, in this embodiment, the emulsion is sterile.

This invention also relates to an oil-in-water emulsion as here above described, further comprising an immunosuppressive agent, preferably cyclosporine, sirolimus or tacrolimus.

Another object of this invention is a pre-concentrate of the therapeutic oil-in-water emulsion of the invention and a process for manufacturing said pre-concentrate. According to this invention, a pre-concentrate is defined as an emulsion having an amount of oil higher than the amount of oil of the therapeutic emulsion administered to a patient. In a first embodiment, the amount of oil in the pre-concentrate is of at least 3% v/v. In a second embodiment, the amount of oil in the pre-concentrate is of at least 6% v/v. In a third embodiment, the amount of oil in the pre-concentrate is of at least 10% v/v., preferably of at least 20% v/v, more preferably of at least 30% v/v.

The pre-concentrate may be in a liquid form or in a gel form, or in any form suitable in view of its further dilution with water.

According to an embodiment, the pre-concentrate of ophthalmic oil-in-water emulsion according to the present invention may be sterilized, for example, by heat, such as by autoclaving, or by filtering or filtration, or by irradiation, or by gas sterilization. In another embodiment, the concentrate of the ophthalmic emulsion is prepared in an aseptic manner.

This invention also relates to a process for manufacturing a pre-concentrate of a therapeutic oil-in-water emulsion comprising the steps of emulsifying/mixing the oil phase with an aqueous phase and with surfactant(s), wherein the non-steroidal anti-inflammatory drug is dissolved in the oil phase. The process for manufacturing said pre-concentrate comprises emulsifying an amount of oil with an aqueous phase and with suitable surfactants, in order to obtain an emulsion having an amount in oil higher than the amount in oil of the corresponding emulsion to be administered for therapeutic purposes.

Before beginning the manufacturing process, the therapeutic oil-in-water emulsion is designed, with a wished concentration of oil, the type of oil (suitable for ophthalmic use, such as for example castor oil, MCT . . . ), the type of elements needed for emulsification such as surfactants for example, and one or more NSAID. The concentration of the concentrate is then decided, depending on the industrial volumes needed.

This invention also relates to a process for manufacturing a therapeutic oil-in-water emulsion comprising (1) manufacturing a pre-concentrate of an ophthalmic oil in water emulsion, said pre-concentrate having a content in oil of at least 3% v/v, preferably of 10% v/v or more, more preferably of 20% v/v or more, even more preferably of 30% v/v or more by emulsifying/mixing an oil suitable for ophthalmic use selected in the group comprising mineral oil, castor oil and MCT, said oil phase containing one or more NSAID, such as flurbiprofen, ibuprofen or ketoprofen, and preferably containing flurbiprofen, with an aqueous phase comprising a quaternary ammonium halide and with surfactant(s) and then (2) diluting one volume of the resulting pre-concentrate with 2 to 50 volumes of water.

According to an embodiment, the emulsification is such that the droplet size or the distribution of the droplet size in the pre-concentrate is about the same as the droplet size or the distribution of the droplet size of the therapeutic oil-in-water emulsion.

According to an embodiment, the diluting water may comprise additives selected from the group comprising tonicity agents, such as for example NaCl, glycerol or mannitol, viscosifying agents, buffering agents, preservatives, antioxidants or colorants.

According to an embodiment, the diluting water may also comprise a quaternary ammonium halide.

Then, according to the invention, a pre-concentrate of this desired emulsion is produced by mixing the oil suitable for ophthalmic use, with an aqueous phase and with surfactant(s); the average hydrophilic-lipophilic balance (HLB) of the surfactant(s) may advantageously be about equal to the HLB or average HLB emulsion requirement of the oil or oils used in the present compositions.

An advantage of this invention is to produce large volumes of emulsions without having to scale-up the emulsifying process. This invention relates to a process for manufacturing a therapeutic oil-in-water emulsion according to the invention, comprising manufacturing a concentrate according to the above-mentioned process and then diluting said concentrate, by mixing 1 volume of concentrate with 2 to 50 volumes of water, to obtain a final therapeutic emulsion having an oil content of 5% v/v of less, preferably of 3% v/v or less, more preferably of 2% v/v or less, even more preferably of 1% v/v or less.

This invention also relates to a method for the treatment of ocular diseases or conditions consisting in the administration to a patient of an ophthalmic emulsion prepared from a pre-concentrate, according to the above described process.

The invention also relates to oil-in-water emulsions obtainable by the process of the invention, i.e. by manufacturing a concentrate including at least one NSAID such as for example, ibuprofen, ketoprofen or flurbiprofen, and then diluting said concentrate with 2 to 50 volumes of water, said water optionally comprising additives, such as for example tonicity agents, viscosifying agents, buffering agents, preservatives, antioxidants or colorants.

One advantage of the invention is that the oil-in-water emulsions obtained by dilution of the concentrates are formed with reduced energy input.

The following examples and figures illustrate the invention and should not be interpreted in any way as reducing the scope of this invention.

EXAMPLES

Example 1

Example of Formulation of an Oil-in-Water Emulsion (Table 1)

TABLE 1

| PHASE | INGREDIENT | FUNCTION | CONC % w/w |
|---|---|---|---|
| Oily phase | Flurbiprofen anhydride | Active Ingredient | 0.048% |
| | Medium-Chain Triglycerides | Oily agent | 4.00% |
| | Tyloxapol | Surfactant | 0.30% |
| Aqueous phase | BAK C16 (cetalkonium chloride) | Cationic surfactant | 0.005% |
| | Sorbitan monolaurate | Surfactant | 0.1% |
| | Glycerin | Tonicity agent | 2.5% |
| | Water | Diluent | 93.047% |

Example 2

Stability of the Above-Described Emulsion (Table 2)

The stability of the autoclaved emulsion at 80° C. (pH, Zeta potential, mean droplet size, osmolality and flurbiprofen concentration) was monitored for 15 days.

TABLE 2

| | T0 | 7 days | 15 days |
|---|---|---|---|
| Zeta potential (mV) | 27.6 | 24.5 | 22.6 |
| pH | 5.41 | 4.44 | 4.41 |
| Mean droplet size (nm) | 187 | 185 | 202 |
| Osmolality (mOsm/kg) | 313 | 321 | 322 |
| Flurbiprofen concentration (% of theoretical) | 100% | Stable | Stable |

Example 3

In Vivo Study, Flurbiprofen Treatment

Forty-five (45) pigmented rabbits were divided into three groups of fifteen animals corresponding to three treatments with five time-points each (0.5, 1, 2, 4 and 6 hours after administration). All animals were treated with a 50 µl single instillation in each eye of 50 µl of flurbiprofen at 0.03% w/w to the total weight of the composition (cationic emulsion, cationic micelle and marketed solution).

At the respective time-points aqueous humor was sampled from both eyes for flurbiprofen determination.

For this in vivo study, the emulsion and the micelle are as described in Table 3 and Table 4. Ocufen® is an ophthalmic solution containing excipients such as buffer citrate (pH 6.45); edetate disodium; polyvinyl alcohol (1.4%); potassium chloride; purified water and sodium chloride. It has a pH of 6.0 to 7.0 and an osmolality of 260-330 mOsm/kg. The multidose version contains 0.005% thimerosal as preservative.

TABLE 3 emulsion of the invention

| | | Emulsion Theoretical content (% w/w) |
|---|---|---|
| Oily phase | Flurbiprofen | 0.03 |
| | MCT | 2.00 |
| | Tyloxapol | 0.10 |
| | Sorbitan monolaurate | 0.05 |
| Aqueous phase | CKC (BAK C16) | 0.005 |
| | Glycerol | 2.50 |
| | Deionised water | qs 100 |

TABLE 4 cationic micelles

| | Cationic micelles Theoretical content (% w/w) |
|---|---|
| Flurbiprofen | 0.03 |
| Cremophor RH40 | 0.10 |
| CKC (BAK C16) | 0.005 |
| Glycerol | 2.50 |
| Deionised water | qs 100 |

Results shown in FIG. 1 evidence that cationic emulsions of the invention improves the ocular bioavailability compared to marketed solution and compared to cationic micelles.

Example 4

Feasibility Study

A feasibility study of cationic oil-in-water (o/w) emulsions containing ibuprofen or ketoprofen was conducted. The emulsions for these compounds were also compared to micellar solutions of ketoprofen.

Ibuprofen and ketoprofen have a carboxylic group in their structures:

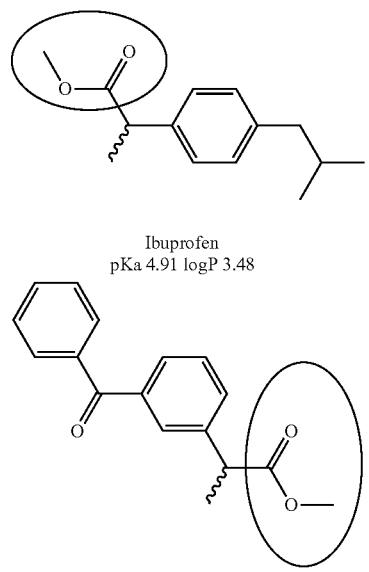

Ibuprofen
pKa 4.91 logP 3.48

Ketoprofen
pKa 4.45 logP 3.55

In order to increase their distribution in oil, emulsions were formulated at a pH<pKa. The molecule being less ionized, their migration to the aqueous phase would be diminished.

Emulsions were also prepared at pH 7.0 in order to respect the physiological pH and also to improve the tolerance and the toxicity of the product.

The emulsions were evaluated at the targeted concentrations of 0.35 to 0.7% for ibuprofen and 0.43 to 0.56% for ketoprofen. The formulas and their characterization are described in detail below:

A. Emulsions Containing Ibuprofen

Formulas

Compositions (% w/w) of the emulsions containing ibuprofen are listed in Table 6. Each of the compositions contains deionised water in sufficient quantity to reach 100% w/w.

Characterization

The emulsion parameters, e.g., pH, zeta potential, osmolality, droplet size, and polydispersity index, were determined. This data is presented in Table 7.

B. Emulsions/Micellar Solutions Containing Ketoprofen

Formulas

Compositions (% w/w) of the emulsions containing ketoprofen are listed in Tables 8a and 8b. Each of the compositions contains deionised water in sufficient quantity to reach 100% w/w. The micellar solutions are listed in Table 9.

Characterization

The emulsion and solution parameters, e.g., pH, zeta potential, osmolality, droplet size, and polydispersity index, were determined. This data is presented in Table 10.

All the emulsions were prepared in a range of pH from 3.00 to 7.00, i.e., from less than their pKa to the physiological pH. Emulsions at pH 3.00 were totally stable during the sterilization step and presented very good characteristics such as a small monomodal mean droplet size distribution (around 100-150 nm) and positive zeta potentials.

An increase in the pH adjustment led to higher droplet size distribution which also became multimodal with micronic populations. It was also observed that higher the adjusted pH was, lower the zeta potential was.

Therefore, at physiological pH, when ibuprofen and ketoprofen are introduced in o/w emulsions, an irreversible destabilization of the vehicle during the sterilization by autoclave was observed.

TABLE 6

Composition of emulsions

| Emulsion Name | API Ibuprofen (% w/w) | Oil MCT (% w/w) | Co-solvant PEG 300 (% w/w) | Co-solvant Cremophor EL (% w/w) | Emulsifiers Tyloxapol (% w/w) | Emulsifiers Poloxamer 188 (% w/w) | Osmotic agent Glycerin (% w/w) | Cationic agent BAK USP grade (% w/w) |
|---|---|---|---|---|---|---|---|---|
| Z56EM001 | Max sol. | 1.00 | / | / | 0.30 | 0.01 | 2.25 | 0.02 |
| Z56EM002 | 0.50 | 2.00 | 1.00 | / | | | 2.35 | |
| Z56EM003 | 0.35 | 2.00 | | 1.00 | | | | |
| Z56EM004 | 0.60 | 2.00 | 1.00 | 1.00 | | | | |
| Z56EM005 | 0.70 | / | 2.00 | 1.00 | | | | |

/: not relevant;
MCT: medium chain triglycerides;
PEG: Polyethylene glycol

TABLE 7

Emulsion parameters after preparation

| Emulsion | Aspect | pH Natural | pH Adjust. | pH After prep. | Zeta potential (mV) | Osmolality (mOsm/kg) | Droplet size (nm) | Polydispersity index |
|---|---|---|---|---|---|---|---|---|
| Z56EM001 | 13 | 3.25 | 3.25 | 3.34 | +17.6 | 244 | 119 (100%) | 0.105 |
| | 1 | | 7.00 | NA | NA | NA | NA | NA |
| | 1 | | NA | 5.03 | NA | NA | NA | NA |
| Z56EM002 | 13 | 3.49 | 3.03 | 3.04 | +16.8 | 315 | 146 (98%) | 0.116 |
| | 1 | | 5.04 | NA | NA | NA | NA | NA |
| | 3/11 | | 6.01 | 5.93 | +19.0 | 325 | 3709 (100%) | 0.010 |
| | 11 | | 7.02 | 7.15 | +8.9 | 356 | 517 (100%) | 0.029 |
| Z56EM003 | 13 | 3.81 | 3.03 | 3.08 | +14.4 | 286 | 86 (100%) | 0.055 |
| | 3/11 | | 4.98 | 4.86 | +16.0 | 285 | 190 (87%) | 0.282 |
| | 3/11 | | 5.98 | 5.88 | +13.9 | 290 | 214 (97%) | 0.242 |
| | 3/11 | | 7.02 | 7.03 | +9.5 | 315 | 204 (73%) | 0.383 |
| Z56EM004 | 13 | 3.66 | 3.02 | 3.08 | +13.7 | 330 | 80 (100%) | 0.040 |
| | 3/11 | | 4.99 | 4.72 | +14.8 | 331 | 154 (100%) | 0.175 |
| | 3/11 | | 6.02 | 5.86 | +10.6 | 343 | 139 (60%) | 0.291 |
| | 3/11 | | 7.00 | 6.98 | +5.5 | 378 | 232 (85%) | 0.347 |
| Z56EM005 | 13 | 3.50 | 3.01 | 3.01 | NA | 382 | 76 (100%) | 0.222 |
| | 5/11 | | 5.00 | NA | NA | NA | NA | NA |
| | 5/11 | | 5.98 | NA | NA | NA | NA | NA |
| | transparent | | 6.99 | 7.02 | −15.8 | 441 | 13 (83%) 712 (16%) | 0.314 |

Percentages in parantheses correspond to the peak intensity.
NA: not assessed.

TABLE 8a

Composition of emulsions

| Emulsion Name | API Ketoprofen (% w/w) | Oil MCT (% w/w) | Co-solvant PEG 300 (% w/w) | Co-solvant PEG400 (% w/w) | Emulsifiers Tyloxapol (% w/w) | Emulsifiers Poloxamer 188 (% w/w) | Osmotic agent Glycerin (% w/w) | Cationic agent BAK USP grade (% w/w) |
|---|---|---|---|---|---|---|---|---|
| Z61EM001 | 0.56 | 2.00 | 1.00 | / | 0.30 | 0.01 | 2.35 | 0.02 |
| Z61EM002 | 0.56 | 2.00 | / | 1.00 | | | | |

/: not relevant;
MCT: medium chain triglycerides;
PEG: polyethylene glycol

TABLE 8b

Composition of emulsions

| Emulsion Name | API | Oil | Co-solvant | | Emulsifiers | | Osmotic agent | Cationic agent |
|---|---|---|---|---|---|---|---|---|
| | Ketoprofen (% w/w) | MCT (% w/w) | Polysorbate 80 (% w/w) | Cremophor EL (% w/w) | Tyloxapol (% w/w) | Poloxamer 188 (% w/w) | Glycerin (% w/w) | BAK USP grade (% w/w) |
| Z61EM003 | 0.43 | 2.00 | / | 1.00 | 0.30 | 0.01 | 2.35 | 0.02 |
| Z61EM004 | 0.43 | 2.00 | 1.00 | / | | | | |

/: not relevant
MCT: medium chain triglycerides

TABLE 9

Composition of solutions

| Solution Name | API | Surfactants | | Osmotic agent | Water 5 mM phosphate |
|---|---|---|---|---|---|
| | Ketoprofen (% w/w) | Polysorbate 80 (% w/w) | Cremophor EL (% w/w) | NaCl (% w/w) | pH 7 (% w/w) |
| Z61SOL005 | 0.43 | / | 1.00 | 0.85 | q.s. 100% |
| Z61SOL006 | 0.43 | 1.00 | / | | |

/: not relevant

TABLE 10

Emulsion and solution parameters after preparation

| Emulsion | Aspect | pH Natural | pH Adjust. | pH After prep. | Zeta potential (mV) | Osmolality (mOsm/kg) | Droplet size (nm) | Polydispersity index |
|---|---|---|---|---|---|---|---|---|
| Z61EM001 | 11 | 3.23 | 3.02 | 3.01 | +19.4 | 330 | 150 (100%) | 0.123 |
| | 3/11 | | 6.98 | 6.80 | +11.0 | 372 | 599 (51%) | 0.314 |
| Z61EM002 | 11 | 3.24 | 3.00 | 3.00 | +18.7 | 326 | 163 (94%) | 0.157 |
| | 3/11 | | 6.97 | 6.88 | +10.2 | 368 | 640 (98%) | 0.111 |
| Z61EM003 | 11 | 3.43 | 3.02 | 3.06 | +12.6 | 291 | 117 (100%) | 0.102 |
| | 7/11 | | 7.03 | 7.04 | +5.9 | 324 | 297 (100%) | 0.353 |
| Z61EM004 | 1 | 3.49 | 2.99 | NA | NA | NA | NA | NA |
| | 1 | | 6.99 | NA | NA | NA | NA | NA |
| Z61SOL005 | White, opaque, sedimentation | 4.65 | / | 4.65 | / | 295 | 17 (100%) + >10 μm | 1.000 |
| Z61SOL006 | Sedimentation during preparation | NA | NA | NA | NA | NA | NA | NA |

Percentage in brackets corresponds to the peak intensity
NA: not assessed
/: not relevant It should be noted that, for these emulsions containing either ibuprofen or ketoprofen and prepared at a pH lower than 7, emulsions pH remained stable during the sterilization step.

Concerning the preparation of micellar solutions containing ketoprofen, the one containing cremophor EL as a surfactant was not feasible. Although the micellar solution containing poloxamer 188 as a surfactant had acceptable characteristics after autoclave, a drug precipitation was observed over time.

Based on this feasibility study, it may be concluded that an emulsion is a better vehicle to formulate non-steroidal anti-inflammatory drugs such as for example ibuprofen or ketoprofen than a solution, for example a micellar solution.

These NSAID containing emulsions should be prepared at a pH lower than 7.00, preferably lower than 5.

In the case of ibuprofen or ketoprofen, emulsions could be obtained at pH 5.00 or 6.00 but their phyisco-chemical characteristics are not totally acceptable.

This method is also adapted to flurbiprofen, a more lipophilic compound.

The invention claimed is:

1. An oil-in-water emulsion comprising a non-steroidal anti-inflammatory drug and benzyl dimethyl ammonium chloride or bromide, in which the nitrogen atom is substituted by an alkyl group having at least 12 carbon atoms, wherein
said emulsion being prepared at pH lower than 7 and lower than the pKa of the drug, and then buffered at physiological pH, and
said emulsion keeping a positive zeta potential over time.

2. The oil-in-water emulsion according to claim 1, wherein said non-steroidal anti-inflammatory drug is selected from the group consisting of ketorolac, salicylate, indomethacin, ibuprofen, ketoprofen, flurbiprofen, suprofen, piroxicam, COX2 inhibitors, diclofenac, nimesulide, nepafenac, antineoplastics, cisplatin, mitomycin and fluorouracil.

3. The oil-in-water emulsion according to claim 1, wherein said non-steroidal anti-inflammatory drug is flurbiprofen, ketoprofen and/or ibuprofen.

4. The oil-in-water emulsion according to claim 1, comprising 0.001% to 10% by weight of a non-steroidal anti-inflammatory drug to the total weight of the emulsion.

5. The oil-in-water emulsion according to claim 1, wherein said benzyl dimethyl ammonium chloride or bromide, in which the nitrogen atom is substituted by an alkyl group having at least 12 carbon atoms is C16-alkyl benzyl dimethyl ammonium chloride.

6. The oil-in-water emulsion according to claim 1, said emulsion comprising:
   an oil phase comprising an oil selected from the group consisting of medium chain triglycerides, castor oil, mineral oil, and combinations thereof;
   at least one surfactant selected from the group consisting of tyloxapol, poloxamer, tocopherol polyethylene glycol succinate, sorbitan monolaurate and polysorbate; and
   optionally antioxidants and/or at least one isotonicity agent selected from the group consisting of glycerol, glycerin and mannitol.

7. The oil-in-water emulsion according to claim 1, comprising 0.001 to 0.1% of ammonium halide.

8. The oil-in-water emulsion according to claim 1, said emulsion having a mean droplet size of 100 to 500 nm.

9. The oil-in-water emulsion according to claim 1, said emulsion being preserved.

10. The oil-in-water emulsion according to claim 1, said emulsion being unpreserved.

11. The oil-in-water emulsion according to claim 1, further comprising an immunosuppressive agent.

12. A medicament comprising the oil-in-water emulsion according to claim 1 and a pharmaceutically acceptable excipient.

13. The medicament according to claim 12, in a unitary dosage form.

14. The medicament according to claim 13, wherein the emulsion is sterile.

15. The medicament according to claim 12, wherein the emulsion is sterile.

16. A method for treating an eye disease caused by, associated with or accompanied by inflammatory processes, comprising the step of administering an effective amount of the oil-in-water emulsion according to claim 1 to a subject in need thereof.

17. A method of treating a subject at risk of developing inflammation or developing an inflammatory process from surgery or trauma, comprising the step of applying pre-surgically or immediately post-traumatically an effective amount of the oil-in-water emulsion according to claim 1 to a subject in need thereof.

18. A method of treating inflammation or limiting an inflammatory process comprising the step of administering an effective amount of the oil-in-water emulsion according to claim 1 to a subject in need thereof.

19. The method according to claim 16, wherein said medicament is administrated less than 4 times a day.

20. A process for manufacturing a pre-concentrate of an oil in water emulsion according to claim 1, said pre-concentrate having a content in oil of at least 3% v/v, the process comprising the steps of emulsifying the oil phase with an aqueous phase and with surfactant(s), the non-steroidal anti-inflammatory drug being dissolved in the oil phase.

21. A pre concentrate of a therapeutic oil-in-water emulsion, which is itself an oil-in-water emulsion obtainable by the process of claim 20.

22. A process for manufacturing an ophthalmic oil in water emulsion according to claim 1, comprising:
   (1) manufacturing a pre-concentrate of an ophthalmic oil in water emulsion, said pre-concentrate having a content in oil of at least 3% v/v, comprising the steps of emulsifying an oil suitable for ophthalmic use selected from the group consisting of mineral oil, castor oil and medium chain triglycerides, with an aqueous phase and with surfactant(s) and
   (2) diluting a volume of the resulting pre-concentrate with 2 to 50 volumes of water and benzyl dimethyl ammonium chloride or bromide, in which the nitrogen atom is substituted by an alkyl group having at least 12 carbon atoms.

23. The oil-in-water emulsion according to claim 11, wherein the immunosuppressive agent is cyclosporine.

* * * * *